United States Patent [19]

Brockmann et al.

[11] Patent Number: 4,655,879
[45] Date of Patent: Apr. 7, 1987

[54] GLYCEROL DISTILLATION PROCESS

[75] Inventors: Rolf Brockmann, Langenfeld; Lutz Jeromin, Hilden; Wilhelm Johannisbauer, Erkrath; Helmut Meyer, Duesseldorf-Benrath; Otto Michel, Langenfeld; Juergen Plachenka, Mettmann, all of Fed. Rep. of Germany

[73] Assignee: Henkel Kommanditgesellschaft auf Aktien, Duesseldorf, Fed. Rep. of Germany

[21] Appl. No.: 664,902

[22] Filed: Oct. 26, 1984

[30] Foreign Application Priority Data

Oct. 28, 1983 [DE] Fed. Rep. of Germany ....... 3339051

[51] Int. Cl.$^4$ .......................... B01D 3/34; B01D 1/22
[52] U.S. Cl. .......................... 203/37; 203/49; 203/80; 203/87; 203/98; 203/99; 203/DIG. 19; 203/89; 202/186; 202/205; 202/236; 568/854; 568/869; 159/49; 159/5
[58] Field of Search .......................... 203/37, 49, 31, 41, 203/36, 98, 80, 87, DIG. 19, 99, 73, 89; 435/159; 502/418; 568/854, 869; 210/694; 202/205, 186, 236; 159/49, 5

[56] References Cited

U.S. PATENT DOCUMENTS

| | | | |
|---|---|---|---|
| 1,357,138 | 10/1920 | Bassett | 568/869 |
| 1,474,750 | 11/1923 | Willkie | 203/37 |
| 1,936,497 | 11/1933 | Carothers et al. | 568/869 |
| 2,578,816 | 12/1951 | Lofdahl et al. | 568/869 |
| 2,960,447 | 11/1960 | Anderson et al. | 203/37 |
| 4,009,188 | 2/1977 | Heim et al. | 203/73 |
| 4,225,394 | 9/1980 | Cox et al. | 203/37 |

FOREIGN PATENT DOCUMENTS

| | | | |
|---|---|---|---|
| 0246932 | 9/1963 | Australia | 568/869 |
| 0278651 | 9/1964 | Australia | 568/869 |
| 0674001 | 11/1963 | Canada | 568/869 |
| 1138886 | 6/1957 | France | |
| 0278703 | 12/1928 | United Kingdom | 568/869 |
| 0737570 | 9/1955 | United Kingdom | 568/869 |

OTHER PUBLICATIONS

D'Souza, "The Importance of Glycerol in the Fatty Acid Industry", Journal of the American Oil Chemists Society, vol. 56, pp. 812A–819A (1979).
Stromquist et al., "C. P. Glycerol by Ion Exchange", Industrial and Engineering Chemistry, vol. 53, pp. 1065–1070 (1951).
Ziels, "Recovery and Purification of Glycerol", The Journal of the American Oil Chemists Society, vol. 33, pp. 556–565 (1956).
Chemical Abstract 72:1970 42752p "Preparation of Alpha-Diamines from Epoxides".

Primary Examiner—S. Leon Bashore
Assistant Examiner—V. Manoharan
Attorney, Agent, or Firm—Ernest G. Szoke; Henry E. Millson, Jr.; Mark A. Greenfield

[57] ABSTRACT

An improved process for purification of glycerol obtained from natural sources comprising alkalizing a glycerol-containing crude mixture in the presence of air for oxidation, evaporating the mixture in a thin-layer evaporator with redistillation of the residue, rectification and reevaporation in a packed column characterized by low-pressure-loss plates with a falling-film evaporator designed for internal and external partial condensation and to separate off unwanted constituents of the mixture, bleaching the product with activated carbon and separating the bleach in known manner.

3 Claims, 1 Drawing Figure

GLYCEROL DISTILLATION PROCESS

BACKGROUND OF THE INVENTION

1. Field of the Invention

The purification of glycerol obtained from naturally occurring fats and oils by an improved distillation process.

2. Statement of the Relevant Art

Glycerol (propane-1,2,3-triol) is the most important of the trihydric alcohols. It is present as its esters in all animal or vegetable fats and oils and is obtained from them as a by-product of the saponification process during soap manufacture. Although glycerol is also synthesized from petrochemicals, this invention is concerned only with the purification of glycerol obtained from naturally occurring fats and oils.

Glycerol is formed during the transesterification, splitting or saponification of natural oils and fats, by saponification with alkali or by high pressure hydrolysis, and—depending on the saponification process—contains relatively large quantities of water, inorganic salts, fats, low molecular weight organic compounds and also higher glycerol oligomers and polymers.

The organic impurities accumulating in the crude glycerol consist primarily of fats and glycerol-like compounds formed by bacterial or chemical decomposition, such as propane-1,2-diol and propane-1,3-diol or even other components, such as glycerol methyl ethers which barely differ from glycerol in their physical properties (boiling point, refractive index) and which interfere seriously with the purification process because they are distilled together with glycerol in conventional columns having a small number of theoretical plates. Some of these impurities are responsible for the undesirable discoloration and poor color stability of the crude glycerol; accordingly, their separation is absolutely essential.

One feature common to all processes carried out on an industrial scale for extracting purified glycerol obtained from natural fats and oils is that production of high purity glycerol requires a crude mixture of which the organic impurity content (mong content) amounts to $\leq 1\%$ by weight and from which fat, soap and other organic constituents have been removed. To this end, the fats are saponified with calcium hydroxide solution or by the lime-soda (calcium-sodium hydroxide) process in an elaborate chemical prepurification stage and are filtered off as far as possible in the form of soaps. Further separation, particularly to remove inorganic impurities, is carried out by distillation. Columns in which the plates produce a high pressure loss are used in the rectification stage. In order to obtain adequate separation of the various components, the sump temperatures have to be correspondingly high. Limits are imposed on this process parameter by the fact that glycerol begins to split off water and to decompose and polymerize at temperatures of the order of 180° C. Crude glycerol is processed in various ways, depending on its salt content. Crude glycerol of low salt content may be directly purified using ion exchangers whereas crude glycerol of high salt content has to be pretreated by distillation to remove the salt. To obtain pure glycerol of the requisite commercial quality, distillation is followed by treatment with ion exchangers, for which purpose the concentrated glycerol has to be rediluted. Both processes are very expensive in terms of apparatus and energy consumption, cannot always be carried out continuously and are accompanied by considerable losses of glycerol. In order to separate glycerol by distillation from higher boiling impurities as well, the mixture has to be additionally subjected to severe thermal stressing which produces further losses of glycerol and more decomposition products.

SUMMARY OF THE INVENTION

The present invention provides an improved process for the non-degenerative distillation of glycerol, in which glycerol derived from natural fats and oils is continuously separated from its impurities, particularly salts, water and organic contaminants affecting its chemical and physical properties, without having to be subjected to intense thermal stressing. The yields amount to 90% and higher and the quality of the glycerol is at least of a food and cosmetic standard. Preferably, the glycerol is purified to pharmaceutical standards such as that set by the U.S. Pharmacopeia, Deutsche Industrienorm No. 55,967, or Europharm III.

The present invention thus relates to a process for the improved purification by distillation of glycerol obtained by the transesterification, splitting or saponification of natural fats and oils. The process comprises alkalizing a glycerol-containing crude mixture in the presence of air for oxidation, evaporating the mixture in a thin-layer evaporator with redistillation of the residue, rectification and reevaporation in a packed column having low-pressure-loss plates with a falling film evaporator designed for internal and external partial condensation and to separate off unwanted constituents of the mixture, bleaching the product with activated carbon and separating the carbon in known manner.

The process according to the invention enables high salt, low salt, or salt free crude glycerols to be purified continuously. It may also be used for the purification of crude glycerols from alkaline saponification bottoms which contain a high percentage of fatty compounds (mong content $\geq 3\%$ by weight), have a high salt content ($\geq 6\%$ by weight) and contain up to 10% by weight of water. There is no need for chemical pre-purification, even in the case of low quality crude glycerols and where even the most stringent quality requirements have to be satisfied. In addition, predrying has only to be carried out down to 10% by weight of water, which may still be done at normal pressure without having to apply vacuum. Through the application of new technologies in the field of distillation and rectification, such as the combination of thin-layer and falling-film evaporators and packed columns with low-pressure-loss plates, separation efficiency is high despite relatively low sump temperatures, enabling the glycerol to be very carefully treated and losses through decomposition reactions to be avoided. Through the integration of various process steps, such as the separation of main runnings, first runnings, residue and sump, into a unified process, separation of the glycerol takes place under optimal conditions both with regard to apparatus and also to energy consumption. The yields amount to between 90 and 95% of the glycerol processed. The quality of the product may be regulated according to requirements, the yield even for high purity glycerol still exceeding 90%, depending on the quality of the crude glycerol starting material.

The packed column used in the process according to the invention is equipped with two evaporators and gives a twice distilled end product in one process step. The low-pressure-loss plates provide for a high number of separation stages in that process step and lead to nondegenerative separation of the fats and the glycerol-like compounds (1,2- and 1,3-propane diol and also glycerolmethyl ethers), which was not possible in conventional columns because of the inadequate number of separation stages responsible for the high pressure loss per separation stage and the resulting severe thermal stressing of the glycerol.

BRIEF DESCRIPTION OF THE DRAWING

The FIGURE is a flow chart of the process according to this invention, for the non-degenerative purification of glycerol by distillation.

DETAILED DESCRIPTION OF THE INVENTION

Figure 1:
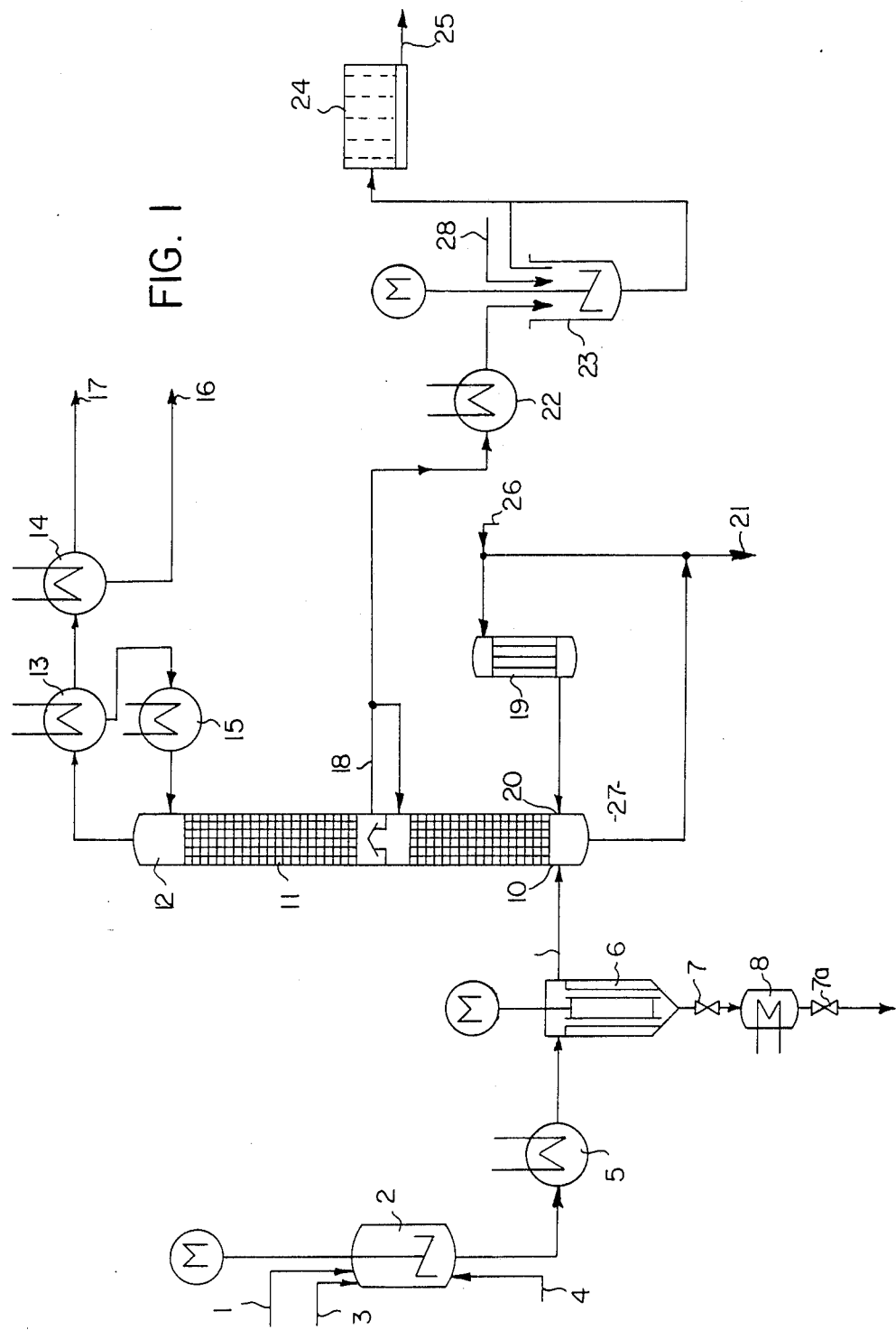

Other than in the operating examples, or where otherwise indicated, all numbers expressing quantities of ingredients or reaction conditions used herein are to be understood as modified in all instances by the term "about".

The process of this invention provides an improved purification of crude glycerol by distillation. The crude glycerol may be obtained by the transesterification, hydrolysis and saponification of natural fats and oils. The successive process steps are evaporation, rectification, bleaching, and separation of the bleaching agent.

The specific steps of this process are as follows:

(a) crude glycerol containing up to 10% by weight of water—without predrying and chemical prepurification—is alkalized for 1 hour at 90° to 100° C. with an aqueous alkali hydroxide solution in a stirrer-equipped vessel, followed by the addition of 10 N/m$^3$ of air/m$^3$ of crude glycerol;

(b) the resulting mixture is optionally preheated, and then is distilled at 165°–180° C./10–20 mbar in a thin-layer evaporator comprising mechanically driven wiper blades, the high boiling constituents being discharged through a lock into a residue receiver in which they undergo additional distillation;

(c) the vapors from the evaporator pass through a drop separator into the lower part of a packed column comprising low-pressure-loss plates (i.e., with a pressure loss of at most 1 mbar/theoretical separation stage at a comparable air velocity of 2 m/s) and flow through that column, at least seven theoretical separation stages being present;

(d) the vapors of the column are partially deposited in a first condenser at 80° to 90° C. under a head pressure of 5 to 10 mbars, the rest being condensed at 20° to 30° C. in a second condenser, the condensate of the second condenser corresponding to approximately 1% of the quantity of crude glycerol used;

(e) the condensate from the first condenser is cooled by 30° to 50° C. and returned to the head of the column, optionally first passing through a reflux condenser;

(f) the main product runnings is continuously removed from the column as a liquid sidestream at a height of approximately $\frac{1}{3}$ of the height of the column, a partial stream being returned to the column immediately beneath the point of removal either at the same temperature or cooled by 20° to 40° C.;

(g) the rest of the main product runnings is cooled to 80° to 90° C. optionally by passing through a third condenser and after the addition of activated carbon bleaching agent in a quantity of 0.1 to 0.3% by weight, is stirred under nitrogen in a vessel for 15 to 30 minutes at 80° to 90° C. and passed through a frame filter press to separate the bleaching agent;

(h) bottom runnings are drawn off from the bottom of the sump and are evaporated in a falling-film evaporator at temperatures in the range about 150° to 180° C. after which the vapors are returned to the sump of the column;

(i) a small partial stream of approximately 1% of the quantity of crude glycerol used is continuously removed from the sump of the column and (j) the vapors deposited in the second condenser, optionally together with the sump discharge of the column, are further processed or partly recycled in another run.

Variant embodiments of the foregoing process include:

(1) introducing 2 to 4 kg of superheated steam per 100 kg of crude glycerol into the column through the falling-film evaporator to react with and decolor the bottom runnings; and (2) using salt free and/or salt containing crude glycerols as starting materials.

It should be understood that in the foregoing and following description, no particular apparatus limitations are intended, other than in the characterization of the low-pressure-loss plates of the packed column. Thus, the first, second, third, and reflux condensers may be any known condensing means. The first and second stirrer equipped vessels may be any known stirring and container means. The thin-layer evaporator may be any known thin-layer evaporator means and the falling-film evaporator may be any known falling-film evaporator means. Any known power or mechanical means may be utilized for introducing or discharging reactants or products, where needed. Heat energy, where required, may be obtained from any known energy source, although it is preferred to conserve heat energy removed during some process steps by recycling it to energy consuming steps. Any known filtering means may be used for separation of the activated carbon bleaching agent, although frame filter presses are preferred. The column itself may be any known column means which is adapted to contain the required low-pressure-loss plates and thereby provide at least seven theoretical separation stages with the indicated minimal pressure loss.

Referring more specifically to the drawing FIGURE, the crude glycerol mixture is introduced at 1 into a first stirrer equipped vessel 2 in which 50% sodium hydroxide or potassium hydroxide is added at 3 to saponify the fats and fatty acids, followed by alkalization at 90° C. for at least one hour, during which air is introduced with stirring at 4 to oxidize reducing components of the mixture.

The reaction mixture thus treated passes through a preheater 5, in which it is heated to approximately 140° C., into a thin layer evaporator 6 in which the glycerol is carefully concentrated by evaporation in vacuo (max. 15 mbars) with mechanical stirring.

The residue containing the soaps formed during alkalization, salts and polymeric glycerols is discharged through a heated upper ballcock 7 at the lower end of the thin-layer evaporator into a similarly heated receiver 8 in which the residue undergoes additional "squeezing out" under the effect of higher temperatures. The receiver 8 is continuously emptied through the similarly heated lower ballcock 7a after the upper ballcock 7 has been shut off and the receiver vented.

The receiver is then preevacuated by a ring pump and the connection between the evaporator 6 and the heated receiver 8 reestablished.

The vapors from the thin-layer evaporator 6 pass through a heated vapor tube 9 into the sump 27 of the packed column 11 at 10. The vapor tube 9 is fitted with separation aids to prevent droplets of liquid from the evaporator 6 from being entrained.

The vapors are rectified as they ascend through the packed column 11. The column is fitted with low-pressure-loss plates so that a high number of separation stages is obtained without the glycerol being decomposed by severe temperature stressing in the sump 27. For a comparable air velocity of at least 2 m/s, the low-pressure-loss plates lead to a pressure loss of at most 1 mbar/theoretical separation stage, at least seven theoretical separation stages being present.

The vapors of the upper separation zone are partly deposited in the first condenser 13 at approximately 85° C. and under a head pressure of at most 10 mbar (dephlegmator). The liquid phase formed is cooled in the reflux condenser 15 and returned to the head 12 of the column 11 (i.e., internal and external partial condensation). The lower boiling components of the vapors leaving the column at its head 12 condense in a second condenser 14 and are run off as first runnings at 16. In addition to glycerol, the first runnings mainly contain esters, fats and glycerol-like compounds. Vapors which are not condensible under the preveiling conditions of pressure and temperature, mainly water, pass uncondensed into a vacuum unit at 17.

Higher boiling components, such as dimeric glycerol and colored constituents, may be separated off from the ascending vapors by at least two theoretical separation stages in the lower third of the column. At the upper end of this part of the column, the entire column reflux is laterally run off at 18 as the main product runnings. Part of the main product runnings passes back into the column at about the same point 18 either with the same temperature or even slightly cooled. This fraction may be regulated and serves to remove the high boiling and colored constituents from the vapor containing good product.

A small quantity of the liquid mixture is continuously removed from the sump 27 at the lower end of the column 11 to counteract an excessive concentration of colored components. The contents of the sump 27 of the column 11 are carefully evaporated in the sump falling-film evaporator 19 at a maximum temperature of 165° C. (second evaporation), the vapors being returned to the sump 27 at point 20 while the residue is collected as sump discharge at 21 and may be recycled, optionally together with the first runnings 16, in another run, shown in the FIGURE in dotted lines. The falling-film evaporator 19 is preferably designed for internal and external partial condensation and to separate off unwanted constituents of the crude glycerol.

The greater part of the main product runnings removed at 18 is cooled in a main condenser 22 and then continuously bleached by adding activated carbon 28 in a second stirrer equipped vessel 23. Bleaching is carried out for 30 minutes at 80° C. with from 0.1 to 0.3% by weight of activated carbon, depending on the quality of the crude glycerol, the glycerol/carbon mixture being placed under a nitrogen blanket. The carbon is removed by means of frame filter presses 24.

The heat removed from the main product runnings in the third condenser 22 for cooling to 80° C. is used to heat the crude product after alkalization in the preheater 5 preceding the thin layer evaporator 6.

Since the stream of condensed first runnings removed at 16 still contains considerable quantities of glycerol, the entire process may be rerun, although without a further alkalization step, optionally together with the sump discharge 21. Any resulting deterioration in color in the main product runnings of the column may be corrected by slightly increasing the quantity of activated carbon used in the bleaching stage. Alternatively, none of the condensed first runnings 16 may be returned to the alkalization vessel.

In cases where the crude glycerol contains less than 5% by weight of water, an improvement in the color of the main product runnings removed at 18 may optionally be obtained by introducing superheated steam at 26 into the head of the falling-film evaporator 19.

The bleached process products which are run off as final runnings and which are obtained at 25 are of excellent quality. The glycerol content amounts to between 99.8 and 99.9%. After bleaching, the products are colorless and clear and have Hazen numbers of from 5 to 10. The product does not contain any salt residues and has a water content of less than 0.1%. With product qualities such as these, a glycerol yield of from 90 to 95% is obtained.

The invention is illustrated by the following Examples, which were carried out with glycerols of various origin.

EXAMPLE 1

Crude glycerol mixture of high salt content from the transesterification of coconut oil; water content 2 to 10%, salt content 4 to 6%, mong content 2 to 3%, was used as the starting material.

EXAMPLE 2

Highly colored, strong-smelling crude glycerol mixture of high salt content from the splitting of a residue accumulating during the splitting of coconut oil; water content 2 to 10%, salt content 6%, mong content 1.5%, was used as the starting material.

Using the crude glycerol mixtures of Examples 1 and 2 in the inventive process, the following values were obtained after bleaching with 0.2% and 0.3% of two types of active carbon.

| Tested Value | Example 1 | Example 2 |
|---|---|---|
| $n_D$ (20° C.): | 1.4737 | 1.4737 |
| Glycerin content (% by weight): | 99.8–99.9 | 99.8–99.9 |
| Hazen No.: | 5 | 5–10 |
| S.V. (% $Na_2O$): | 0.006 | 0.006 |
| S. No.: | 0.11 | 0.11 |
| E. No. (ml N-10 HCl): | 9.2 | 9.2 |
| A. No.: | 0.1 | 0.1 |
| Red substances | | |
| 1st stage: | colorless clear | colorless clear |
| 2nd stage: | yellowish gray | yellow-gray |
| Miscibility water: | colorless clear | colorless clear |
| Water content (% by weight): | 0.07 | 0.07 |
| $Cl^-$: | — | — |
| $SO_4^{--}$: | — | — |
| Yield (%) | 95 | 90 |

We claim:

1. A process for the purification of crude glycerol derived from the transesterification, hydrolysis, and saponification of naturally occurring fats and oils, comprising
- (a) alkalizing crude glycerol containing up to 10% by weight of water without predrying and chemical prepurificaton by mixing with an aqueous alkali hydroxide solution for about 1 hour at about 90°–100° C., followed by the addition of about 10 $N/m^3$ of air per cubic meter of said crude glycerol;
- (b) distilling the alkalized mixture at about 165°–180° C. and about 10–20 mbar and discharging high boiling constituents for additional distillation;
- (c) passing the vapors generated by said distillation into a lower part of a packing column and flowing said vapors upward through said column, said column containing low-pressure-loss plates having a pressure loss of at most 1 mbar/theoretical separation stage at an air velocity of 2 m/s and having at least seven theoretical separation stages;
- (d) partially first condensing the vapors from said column at about 80°–90° C. under a head pressure of about 5–10 mbars, and second condensing the remaining vapors at about 20°–30° C., so that the second condensate corresponds to approximately 1% of the quantity of crude glycerol;
- (e) cooling the first condensate by about 30°–50° C. and returning same to the head of said column;
- (f) continuously removing a main product from said column as a liquid sidestream at a point approximately ⅓ of the height of said column, and returning a partial stream thereof to said column beneath the point of removal;
- (g) cooling the remaining non-returned portion of said main product to about 80°–90° C.; adding about 0.1 to 0.3% by weight of activated charcoal to the said non-returned portion as a bleaching agent and stirring under nitrogen for about 15 to 30 minutures while at about 80°–90° C.; and then removing said bleaching agent;
- (i) drawing off bottom product from the column sump, evaporating said bottom product at temperatures of about 150°–180° C., and returning vapor generated thereby to said sump,
- (j) continuously removing a partial stream of about 1% of the quantity of glycerol being processed from said bottom product before it is evaporated.

2. The process of claim 1 wherein in step (i) said evaporating is by falling-film evaporation of said bottom product.

3. The process of claim 1 or 2 wherein about 2 to 4 kg of superheated steam per 100 kg of glycerol being processed is introduced during the evaporation of step (i).

* * * * *